(12) United States Patent
Oestergaard (10) Patent No.: US 11,672,912 B2
(45) Date of Patent: Jun. 13, 2023

(54) CARTRIDGE HOLDER ASSEMBLY FOR DRUG DELIVERY DEVICE

(71) Applicant: Novo Nordisk A/S, Bagsvaerd (DK)

(72) Inventor: Brian Oestergaard, Graested (DK)

(73) Assignee: Novo Nordisk A/S, Bagsvaerd (DK)

(*) Notice: Subject to any disclaimer, the term of this patent is extended or adjusted under 35 U.S.C. 154(b) by 517 days.

(21) Appl. No.: 15/560,197

(22) PCT Filed: Mar. 30, 2016

(86) PCT No.: PCT/EP2016/056907
§ 371 (c)(1),
(2) Date: Sep. 21, 2017

(87) PCT Pub. No.: WO2016/156387
PCT Pub. Date: Oct. 6, 2016

(65) Prior Publication Data
US 2018/0071458 A1    Mar. 15, 2018

(30) Foreign Application Priority Data
Mar. 31, 2015  (EP) ..................... 15161852

(51) Int. Cl.
*A61M 5/24* (2006.01)
*A61M 5/315* (2006.01)
(52) U.S. Cl.
CPC ............ *A61M 5/24* (2013.01); *A61M 5/3155* (2013.01); *A61M 5/2466* (2013.01);
(Continued)

(58) Field of Classification Search
CPC ............ A61M 5/24; A61M 2005/2407; A61M 2005/2418; A61M 2005/2477;
(Continued)

(56) References Cited

U.S. PATENT DOCUMENTS

| 9,636,276 B2 | 5/2017 | Woolston |
| 10,383,998 B2 | 8/2019 | Allerdings |

(Continued)

FOREIGN PATENT DOCUMENTS

| EP | 1458440 A1 | 9/2004 |
| JP | 2001087387 A | 4/2001 |

(Continued)

*Primary Examiner* — Tiffany Legette
(74) *Attorney, Agent, or Firm* — Wesley Nicolas (57) ABSTRACT

A cartridge holder assembly is provided, comprising an enclosed cartridge, a distal portion and a proximal portion. The enclosed cartridge defines a longitudinal axis and comprises a generally cylindrical main portion, a distal outlet portion having a neck portion with a circumferential shoulder portion, and a proximal portion having an opening surrounded by a circumferential rim. The distal portion comprises a distal support structure engaging the cartridge neck portion and being adapted to support the cartridge against movement in the distal direction, and the proximal portion comprises a proximal support structure engaging the cartridge circumferential rim and being adapted to support the cartridge against movement in the proximal direction. The proximal support structure is essentially non-deformed, and the distal support structure engaging the cartridge neck portion is plastically deformed.

12 Claims, 4 Drawing Sheets

(52) U.S. Cl.
CPC . *A61M 5/31551* (2013.01); *A61M 2005/2407* (2013.01); *A61M 2005/2418* (2013.01); *A61M 2005/2433* (2013.01); *A61M 2005/2485* (2013.01); *A61M 2207/00* (2013.01)

(58) Field of Classification Search
CPC ............ A61M 5/3155; A61M 5/31551; A61M 5/2466; A61M 2005/2433; A61M 2005/2485
See application file for complete search history.

(56) References Cited

U.S. PATENT DOCUMENTS

| | | |
|---|---|---|
| 2007/0021718 A1* | 1/2007 | Burren .................... A61M 5/24 604/110 |
| 2009/0312715 A1 | 12/2009 | Monson et al. |
| 2012/0143143 A1 | 6/2012 | Giambattista et al. |
| 2013/0253432 A1 | 9/2013 | Avery et al. |
| 2014/0142515 A1 | 5/2014 | Jugl et al. |
| 2017/0296751 A1* | 10/2017 | Newton ................ A61M 5/347 |

FOREIGN PATENT DOCUMENTS

| | | |
|---|---|---|
| JP | 2005511152 A | 4/2005 |
| JP | 2014528784 | 10/2014 |

* cited by examiner

CARTRIDGE HOLDER ASSEMBLY FOR DRUG DELIVERY DEVICE

CROSS-REFERENCE TO RELATED APPLICATIONS

This application is a 35 U.S.C. § 371 National Stage application of International Application PCT/EP2016/056907 (published as WO 2016/156387), filed Mar. 30, 2016, which claims priority to European Patent Application 15161852.7, filed Mar. 31, 2015; the contents of which are incorporated herein by reference.

The present invention relates to medical delivery devices adapted for transcutaneous delivery of an amount of drug. In a specific aspect the invention relates to a holder for a drug cartridge to be used in combination with or forming part of a drug delivery device.

BACKGROUND OF THE INVENTION

In the disclosure of the present invention reference is mostly made to the treatment of diabetes by delivery of insulin, however, this is only an exemplary use of the present invention.

Drug delivery devices in the form of drug injection devices have greatly improved the lives of patients who must self-administer drugs and biological agents. Drug injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. While pen-style injection devices are typically cylindrically shaped with a mounted needle protruding from the most distal portion of one end of the device, some devices have other shapes with the needle no longer protruding from the most distal part of an end of the device, e.g. Innovo® and InnoLet® from Novo Nordisk A/S, Bagsværd, Denmark.

Typically, injection devices use a pre-filled cartridge containing the medication of interest, e.g. 1.5 or 3.0 ml of insulin or growth hormone. The cartridge is typically in the form of a generally cylindrical transparent glass cylinder having a distal bottle neck portion with a distal opening closed by a needle pierceable septum and an opposed proximal opening in which an elastomeric piston is received, the piston being arranged to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded.

The part of the injection device receiving and holding the cartridge is traditionally named a cartridge holder and primarily serves to position and firmly hold the cartridge relative to the piston rod of the expelling mechanism. Especially axial fixation is important for dosing accuracy. Correspondingly, the "complete" cartridge holder comprises a cylindrical body portion, a distal portion engaging the distal portion of the cartridge, and a proximal portion engaging the proximal portion of the cartridge. However, typically the term "cartridge holder" is applied to a tubular member integrally forming both the main portion and the distal portion and having a proximal opening through which a cartridge is inserted in a distal direction. Subsequently the cartridge holder with a received cartridge is mounted on the injection device main part (i.e. the part comprising the expelling mechanism) which then engages the cartridge. In this way a cartridge holder assembly is formed.

Alternatively, the cylindrical body portion of the cartridge holder may be formed by a distal tubular extension of the injection device main part in which a cartridge is inserted in a proximal direction, i.e. "front loaded", the cartridge holder being closed by a distal closure means which may e.g. be a simple "plug" portion or a more elaborate actuatable closure mechanism.

In a further alternative the cartridge holder forms a complete stand-alone sub-assembly in which a cartridge is fully enclosed, and which is subsequently mounted on the injection device main part. Such an assembly may also be provided with portions of the expelling mechanism, e.g. a piston rod, which then interfaces with the remaining piston rod driving mechanism, see e.g. EP 1 458 440.

As appears, for a durable injection device the cartridge holder is mounted using releasable coupling means whereas for a disposable pre-filled device the cartridge holder is permanently mounted on the device main part. As a glass cartridge is manufactured with relatively large tolerances, e.g. 0.5 mm for the length, the cartridge holder has to accommodate this variation. For a durable device the cartridge is thus typically held in place axially by elastically deformable means, e.g. a spring or flexible arms as disclosed in US 2012/0143143. US 2009/0312715 discloses a durable cartridge holder comprising a distal centering structure. In contrast, for a disposable device plastically deformed engagement structures can be utilized.

The above-described types of cartridge holders are typically designed to hold a glass cartridge which per se does not comprise coupling means allowing it to be connected directly to an injection device. However, in case a drug cartridge is manufactured from a polymeric material coupling means may be formed integrally with the cartridge per se for which reason the traditional cartridge holder can be dispensed with.

Having regard to the above, it is an object of the present invention to provide components, devices and methods allowing a drug-filled cartridge to be mounted securely and reliably in a drug delivery device in a cost-effective way. It is a specific object of the invention to provide means allowing a drug-filled glass cartridge to be mounted securely and reliably in a disposable drug delivery device in a cost-effective way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a cartridge holder assembly is provided, comprising an enclosed cartridge, a distal portion and a proximal portion. The enclosed cartridge defines a longitudinal axis and comprises a generally cylindrical main portion, a distal outlet portion having a neck portion with a circumferential shoulder portion, and a proximal portion having an opening surrounded by a circumferential rim. The distal portion comprises a distal support structure engaging the cartridge neck portion and being adapted to support the cartridge against movement in the distal direction, and the proximal portion comprises a proximal support structure engaging the cartridge circumferential rim and being adapted to support the cartridge against movement in the proximal direction. The proximal support structure is elastically deformed only, and the distal support structure is plastically deformed. The cartridge may be manufactured from glass. The proximal support structure may essentially be nondeformed, e.g. less than 0.3, less than 0.2 or less than 0.1 mm in the axial direction.

By this arrangement the punctual forces acting on the cartridge during assembly and handling are acting on the inclined circumferential shoulder of the neck portion, this providing that a cartridge can be mounted securely in a cartridge holder in a cost-effective way.

The distal support structure may be in the form of a number of axially oriented rib portions each comprising a proximal free edge adapted to engage the cartridge shoulder portion, at least a portion of the edge being deformed.

The proximal support structure may be in the form of a number of axially oriented rib portions adapted to engage the cartridge rim portion. The proximal support structure may be in the form of a number of circumferential segments adapted to engage the cartridge rim portion.

The distal support structure may be formed integrally with the distal cartridge holder portion and/or the proximal support structure may be formed integrally with the proximal cartridge holder portion.

In an exemplary embodiment the cartridge holder distal and proximal portions are non-removable connected to each other. The cartridge holder distal portion may comprise a tubular main portion in which the cartridge main portion is arranged. The cartridge holder may be generally cylindrical and the proximal portion may comprise a threaded bore adapted to receive a correspondingly threaded piston rod, whereby the proximal portion may form part of a drug expelling mechanism.

The above-described cartridge holder assembly may form part of a drug delivery device comprising drug expelling means for expelling a set dose from the cartridge. The device may be a fixed-dose device or it may comprise dose setting means allowing a user to set a desired dose to be expelled.

In a second aspect of the invention a method of assembling a cartridge holder assembly is provided, the method comprising the steps of: (i) providing a cartridge defining a longitudinal axis and comprising a generally cylindrical main portion, a distal outlet portion having a neck portion with a circumferential shoulder portion, and a proximal portion having an opening surrounded by a circumferential rim, and (ii) providing a distal cartridge holder portion comprising a distal support structure adapted to engage the cartridge neck portion and support the cartridge against movement in the distal direction, and a proximal cartridge holder portion comprising a proximal support structure adapted to engage the cartridge circumferential rim and support the cartridge against movement in the proximal direction, one of the two cartridge holder portions comprising a tubular portion adapted to axially receive the cartridge main portion. The method comprises the further steps of (iii) inserting the cartridge into the tubular portion, and (iv) assembling the distal and proximal cartridge holder portions to thereby plastically deform the distal support structure, the proximal support structure being elastically deformed only. The proximal support structure may essentially be non-deformed.

In a further aspect of the invention a cartridge holder assembly is provided, comprising an enclosed cartridge, a distal portion and a proximal portion. The enclosed cartridge defines a longitudinal axis and comprises a generally cylindrical main portion, a distal outlet portion having a neck portion with a circumferential shoulder portion, and a proximal portion having an opening surrounded by a circumferential rim. The distal portion comprises a distal support structure engaging the cartridge neck portion and being adapted to support the cartridge against movement in the distal direction, and the proximal portion comprises a proximal support structure engaging the cartridge circumferential rim and being adapted to support the cartridge against movement in the proximal direction. The proximal support structure is essentially non-deformed, and the distal support structure is plastically deformed. The cartridge may be manufactured from glass.

By this arrangement the punctual forces acting on the cartridge during assembly is reduced as compared to embodiments in which plastic deformation takes place.

The distal support structure may be in the form of a number of axially oriented rib portions each comprising a proximal free edge adapted to engage the cartridge shoulder portion, at least a portion of the edge being deformed.

The proximal support structure may be in the form of a number of axially oriented rib portions adapted to engage the cartridge rim portion or the proximal support structure may be in the form of a number of circumferential segments adapted to engage the cartridge rim portion.

The distal support structure may be formed integrally with the distal cartridge holder portion and/or the proximal support structure may be formed integrally with the proximal cartridge holder portion.

In an exemplary embodiment the cartridge holder distal and proximal portions are non-removable connected to each other. The cartridge holder distal portion may comprise a tubular main portion in which the cartridge main portion is arranged. The cartridge holder may be generally cylindrical and the proximal portion may comprise a threaded bore adapted to receive a correspondingly threaded piston rod, whereby the proximal portion may form part of a drug expelling mechanism.

The above-described cartridge holder assembly may form part of a drug delivery device comprising drug expelling means for expelling a set dose from the cartridge. The device may be a fixed-dose device or it may comprise dose setting means allowing a user to set a desired dose to be expelled.

In a yet further aspect of the invention a method of assembling a cartridge holder assembly is provided similar to the above-described method, the difference being that the distal and proximal cartridge holder portions are assembled to thereby elastically deform the distal support structure, the proximal support structure being essentially non-deformed.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a "generic" prior art resettable dial-up/dial down automatic drug delivery device will be described, such a device providing the basis for the exemplary embodiment of the present invention.

Figure 1A:
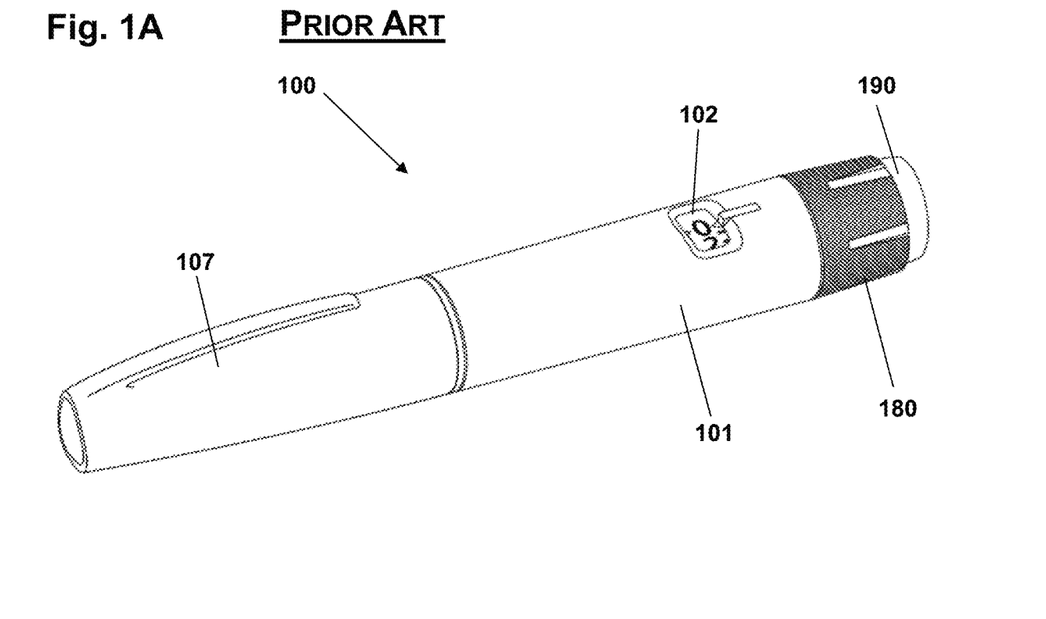
FIGS. 1A and 1B show an embodiment of a drug delivery device.
Figure 1B:
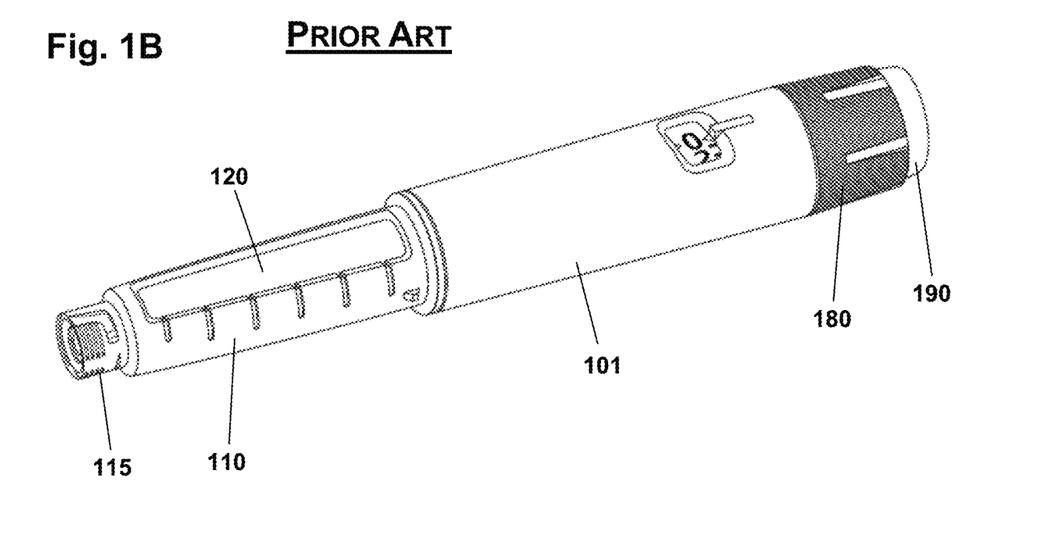

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 120 with a distal needle-penetrable septum is arranged and retained in place by a cartridge holder attached to the proximal portion, the cartridge holder having a pair of opposed openings 111 (not shown) allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the shown embodiment is in the form of a ratchet mechanism. When the user desires to expel the set dose the button is actuated whereby the drive member is brought into engagement with the piston rod drive mechanism and the holding mechanism subsequently released.

Although FIGS. 1A and 1B show a drug delivery device of the pre-filled type, i.e. it is supplied with a pre-mounted cartridge and is to be discarded when the cartridge has been emptied, in alternative embodiments the drug delivery device may be a durable device designed to allow a cartridge assembly to be replaced, e.g. in the form of a cartridge assembly comprising a cartridge mounted in a cartridge holder. Such an assembly may further be provided with a pre-mounted piston rod.

Figure 5:
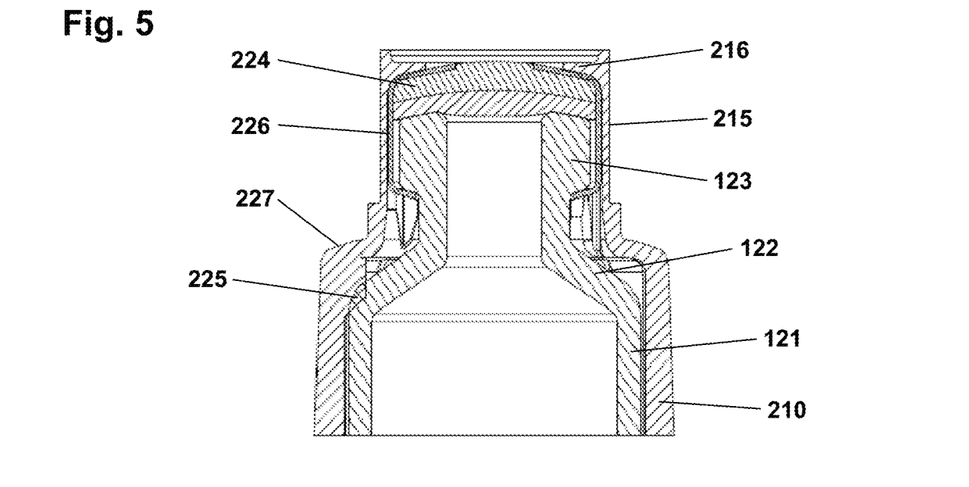
Figure 6:
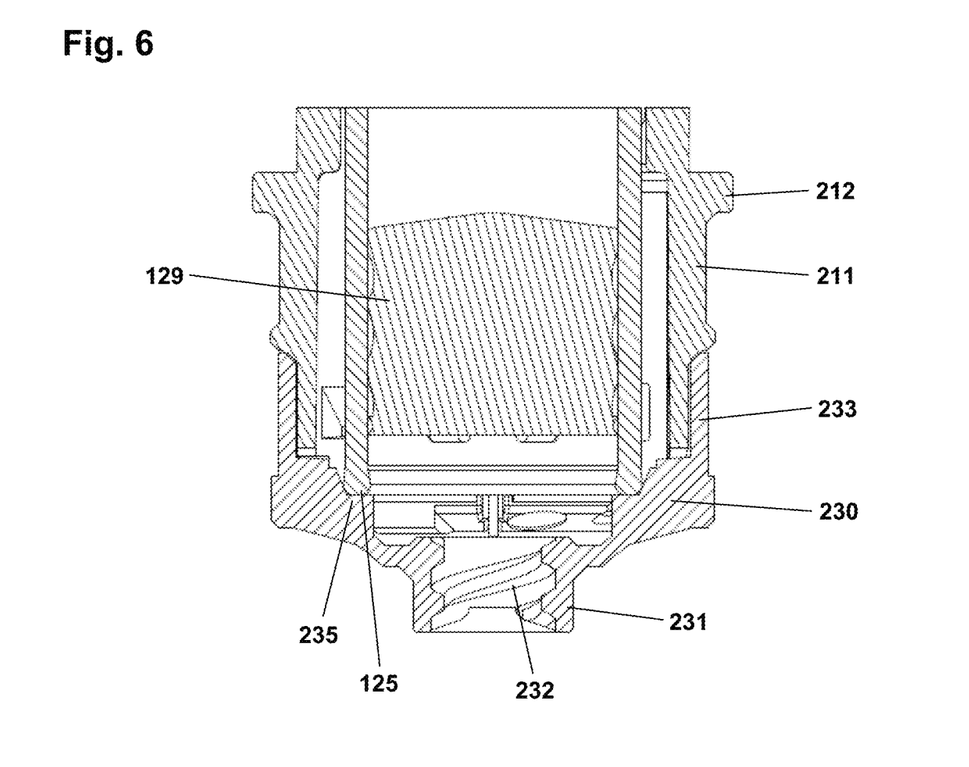

Before turning to an exemplary embodiment of the present invention in FIGS. 5 and 6, the prior art cartridge holder portion of the FIGS. 1A and 1B drug delivery device will be described in greater detail with reference to FIGS. 2-4. As appears, although the cartridge holder in FIGS. 2-6 is shown standing upright it is described utilizing the normal distal-proximal terms used when describing a handheld drug delivery device with a distal outlet.

Figure 2:
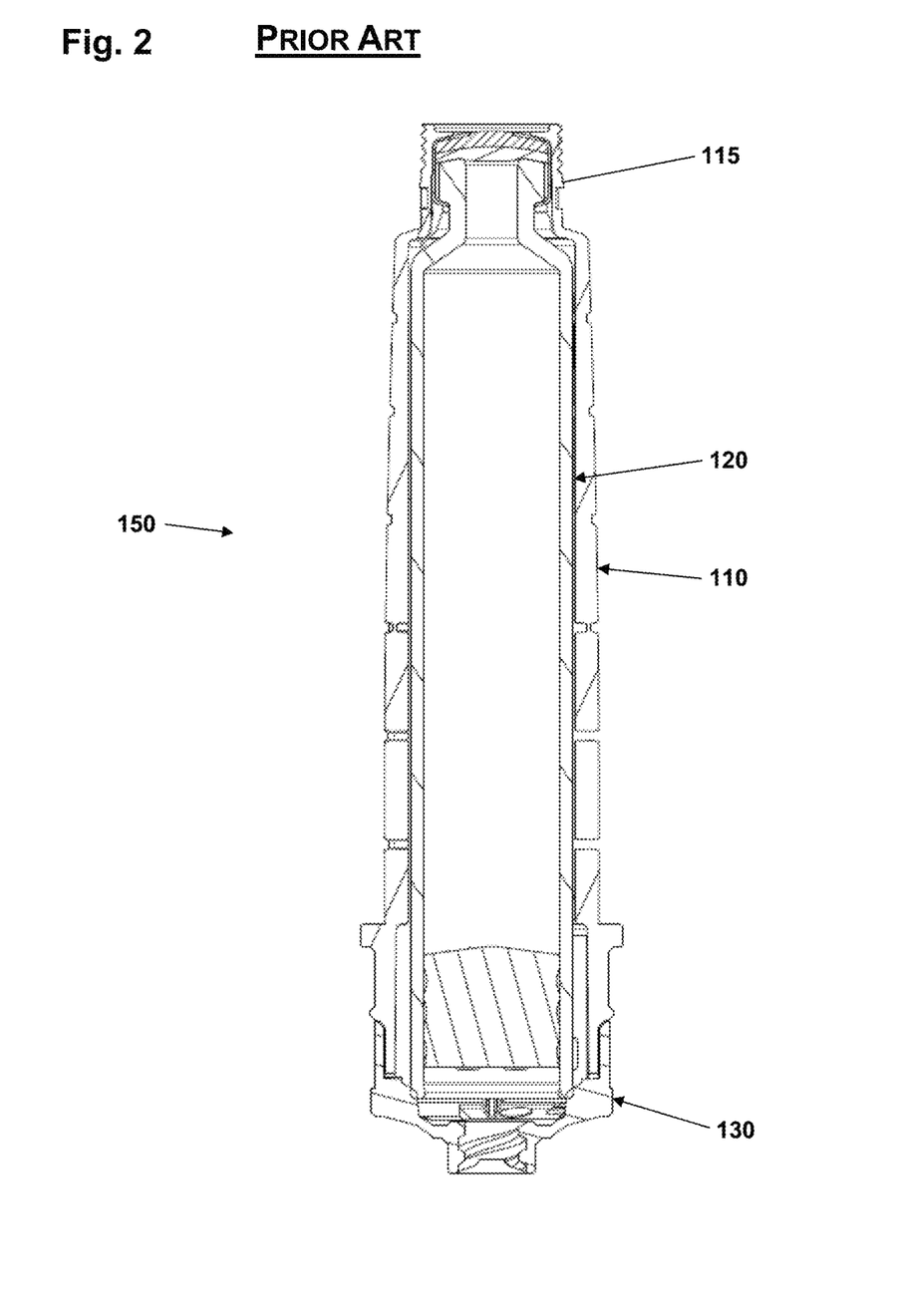
FIG. 2 shows in a cross-sectional view a cartridge holder assembly.

More specifically, FIG. 2 shows in a cross-sectional view a cartridge holder assembly 150 comprising a tubular main member 110 and a thereto attached proximal closure member 130, the two members forming in combination an enclosure in which a drug-filled cartridge 120 is mounted and held in place.

The present invention is intended to be incorporated into a pen device 100 including an expelling structure (not shown).

Figure 3:
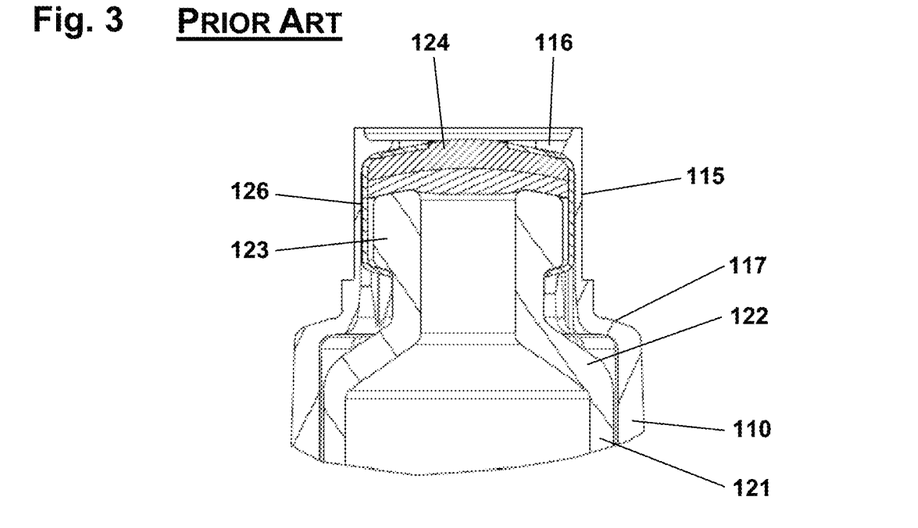
FIG. 3 shows in detail the distal portion of the cartridge holder assembly of FIG. 2.
Figure 4:
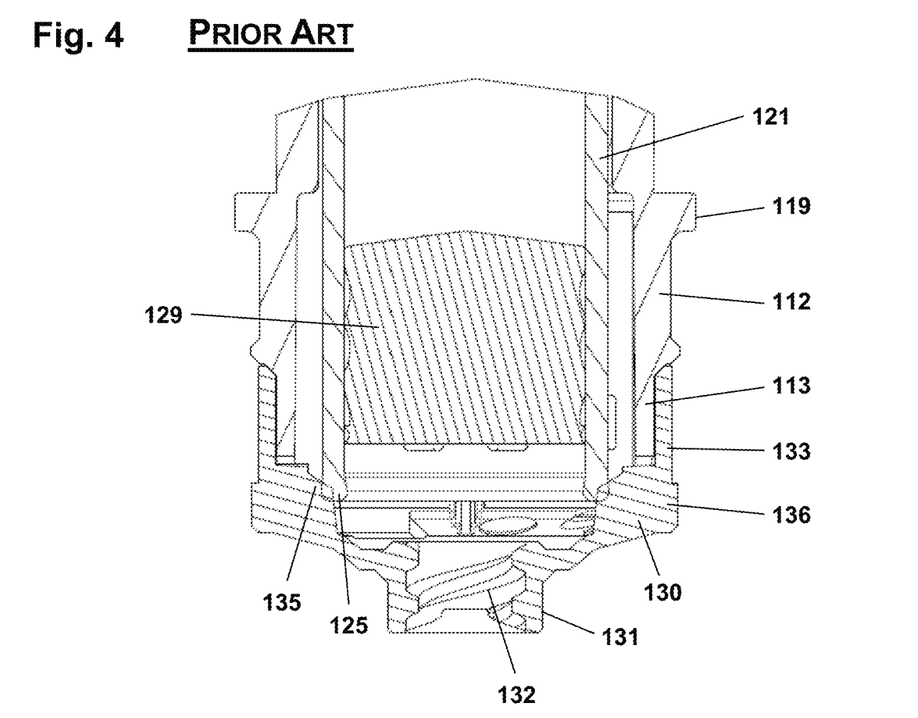
FIG. 4 shows in detail the proximal portion of the cartridge holder assembly of FIG. 2, and FIGS. 5 and 6 show in cross-sectional views the distal respectively the proximal portion of a further cartridge holder assembly.

Turning to FIGS. 3 and 4 the cartridge 120 comprises a tubular main portion 121 with a proximal opening and a circumferential proximal edge (or rim) 125, a distal portion with a distal opening and a circumferential flange 123, as well as a neck portion 122 with inclined shoulders arranged there between. A piston member 129 is slidable received in the tubular main portion. The distal opening is closed with a needle-penetrable septum member 124, which in the shown embodiment comprises two layers of different rubber materials, and which is held in place by a metal cap 126 circumferentially gripping the distal flange portion to thereby hold the septum member in sealing engagement with the cartridge, the metal cap comprising a central opening allowing a needle to penetrate the septum member.

The cartridge holder tubular main member 110 comprises a tubular main portion having an internal diameter allowing a cartridge to be received, a distal coupling portion 115, a neck portion 117 between the distal portion and the main portion, as well as a proximal coupling portion. The distal coupling portion has a generally tubular configuration with outer coupling means 115 (see FIG. 2) for a needle assembly, a central opening surrounded by an inwardly protruding distal flange 116, the distal portion being adapted to receive a distal cap portion of a cartridge in a snug fit. The proximal coupling portion comprises a circumferential outer flange 119, a first circumferential coupling portion 112 adapted to engage the device housing member 101, and a second proximal-most circumferential coupling portion 113 adapted to engage the closure member 130.

The closure member 130 has a general cup-shaped configuration with a bottom portion from which a coupling skirt portion 133 extends distally and from which a central nut portion 131 with an interior thread (132) extends proximally. The coupling skirt portion is adapted to engage the cartridge holder and the nut thread is adapted to receive a threaded piston rod and thus forms part of the expelling mechanism of the drug delivery device. From the bottom portion a number of radial holding ribs 135 (here: four) extend distally, each rib having a free distal edge adapted to engage the cartridge proximal edge. The free edge is inclined to help centre the cartridge. The closure member further comprises circumferential coupling protrusions 136 adapted to engage the device housing member 101.

During assembly the closure member 130 is inserted into the device housing member 101 and the cartridge is inserted into the cartridge holder main member 110, the cartridge metal cap 126 thereby abutting the cartridge holder distal flange 116. Subsequently the cartridge holder main member is inserted into the housing member thereby engaging both the closure member 130 and the housing in locking engagement, the holding ribs 135 thereby engaging the cartridge proximal edge 125. As the distance between the cartridge holder distal flange and the distal edges of the holding ribs is smaller than the minimum length of the cartridge, assembly will result in the ribs being plastically deformed, this ensuring that the cartridge is securely held in its axial position as shown in FIGS. 2 and 4 (showing the deformed rib as overlapping the cartridge edge). The cartridge holder main member and the closure member may be assembled by means of a snap coupling, adhesive, welding or a combination thereof.

As appears, the proximally directed force acting on the glass cartridge is via the metal cap and the septum distributed on the entire circumference of the distal flange 123, whereas the distally directed force acting on the glass cartridge is concentrated in four points corresponding to the four holding ribs 135.

Turning to FIGS. 5 and 6 an exemplary embodiment of the present invention will be described. As appears, the exemplary embodiment of a cartridge holder assembly resamples the above-described prior art assembly and thus comprises a cartridge 120 in combination with a tubular main member 210 with a neck portion 227, and a proximal closure member 230. The exemplary embodiment of the invention differs from the prior art mainly in two aspects. Distally the cartridge holder neck portion 217 (not shown) has been provided with a number of radial distal holding ribs 225 (here: three) extending proximally, each rib having a free proximal inclined edge adapted to engage the inclined cartridge shoulder (neck) portion 122. Proximally the closure member has been modified by making the proximal holding ribs 135 thicker and thereby stronger just as the portion adapted to engage the cartridge proximal rim is no longer inclined, this allowing the cartridge proximal edge to be supported by the closure member. Alternatively, the rim may be supported by wider circumferential segments or by a single surface.

Correspondingly, when the cartridge holder 210, 230 is assembled as described above with reference to FIGS. 2-4 the distal holding ribs 225 are plastically deformed against the cartridge neck portion 122 (FIG. 5 shows the deformed rib as overlapping the cartridge neck) whereas the proximal holding ribs supports the cartridge without plastic deformation. Indeed, to a certain extent the distal ribs will also be elastically deformed. Consequently, the distally directed force acting on the glass cartridge is distributed on the entire circumference of the proximal edge, whereas the proximally directed force is concentrated in three points on the cartridge neck portion 122 corresponding to the three distal holding ribs 225. Although not shown in FIG. 5 the metal cap 226 will normally be slightly spaced from the cartridge holder distal flange 216.

By this new arrangement the punctual forces acting on the glass cartridge has been transferred from the proximal edge to the inclined circumferential shoulder of the neck portion which is expected to better withstand the forces applied during assembly as well as during handling, e.g. when the drug delivery device is dropped from a height. In this way the number of fractured glass cartridges can be reduced.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A cartridge holder assembly comprising:—a cartridge holder and a therein enclosed cartridge forming the cartridge holder assembly, the cartridge holder comprising a distal portion and a proximal portion extending beyond the cartridge proximal end, —the enclosed cartridge defining a longitudinal axis and comprising a generally cylindrical main portion, a distal outlet portion having a neck portion with a circumferential shoulder portion, and a proximal portion having an opening surrounded by a circumferential rim, —the distal portion comprising a distal support structure engaging the cartridge neck portion and being adapted to support the cartridge against movement in a distal direction, and—the proximal portion comprising a proximal support structure engaging the cartridge circumferential rim at a cartridge proximal end and being adapted to support the cartridge against movement in a proximal direction, wherein: —the proximal support structure is elastically deformed only, and—the distal support structure is plastically deformed the cartridge holder assembly attachable to a drug delivery device comprising: a drug expelling structure for expelling a set dose from the cartridge.

2. The cartridge holder assembly as in claim 1, wherein the proximal support structure essentially is non-deformed.

3. The cartridge holder assembly as in claim 1, wherein the proximal support structure is in the form of a number of axially oriented rib portions adapted to engage a portion of the circumferential rim of the enclosed cartridge.

4. The cartridge holder assembly as in claim 1, wherein the proximal support structure is in the form of a number of circumferential segments adapted to engage a circumferential rim portion of the enclosed cartridge.

5. The cartridge holder assembly as in claim 1, wherein the distal support structure is formed integrally with the cartridge holder distal portion of the cartridge holder assembly and/or the proximal support structure is formed integrally with the proximal portion of the cartridge holder assembly.

6. The cartridge holder assembly as in claim 1, wherein the cartridge holder distal portion and the cartridge holder proximal portion of the cartridge holder assembly are non-removably connected to each other.

7. The cartridge holder assembly as in claim 1, wherein the cartridge holder distal portion of the cartridge holder assembly comprises a tubular main portion in which the cylindrical main portion of the cartridge is arranged.

8. The cartridge holder assembly as in claim 1, wherein the cartridge holder assembly is generally cylindrical.

9. The cartridge holder assembly as in claim 1, wherein the cartridge is manufactured from glass.

10. The cartridge holder assembly as in claim 1, wherein the cartridge holder proximal portion comprises a threaded bore.

11. The cartridge holder assembly as in claim 1, the drug delivery device further comprising a dose setting structure.

12. The cartridge holder assembly as in claim 1, wherein the distal support structure is in the form of a number of axially oriented rib portions each comprising a proximal free edge adapted to engage the cartridge shoulder portion, at least a portion of the proximal free edge being deformed.

* * * * *

UNITED STATES PATENT AND TRADEMARK OFFICE
CERTIFICATE OF CORRECTION

| | |
|---|---|
| PATENT NO. | : 11,672,912 B2 |
| APPLICATION NO. | : 15/560197 |
| DATED | : June 13, 2023 |
| INVENTOR(S) | : Oestergaard |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this
Twelfth Day of November, 2024

*Katherine Kelly Vidal*

Katherine Kelly Vidal
*Director of the United States Patent and Trademark Office*